United States Patent van Leusen et al.

Patent Number: 4,647,410
Date of Patent: Mar. 3, 1987

[54] NOVEL 17-SUBSTITUTED STEROIDS

[75] Inventors: Albert M. van Leusen, Groningen; Adriaan M. van Leusen, Winsum, both of Netherlands

[73] Assignee: Gist-Brocades N.V., Delft, Netherlands

[21] Appl. No.: 604,868

[22] Filed: Apr. 27, 1984

[30] Foreign Application Priority Data

Apr. 29, 1983 [EP] European Pat. Off. ........ 83200616.7

[51] Int. Cl.$^4$ .............................................. C07J 43/00
[52] U.S. Cl. ............................ 540/30; 540/36; 540/78; 540/87; 540/114; 260/397.3; 260/397.5; 260/397.45
[58] Field of Search ................... 260/397, 397.1, 397.5, 260/397.3, 397/45

[56] References Cited

U.S. PATENT DOCUMENTS 4,464,302 8/1984 Nedelec et al. ................ 260/397.45

FOREIGN PATENT DOCUMENTS 7672 6/1980 European Pat. Off. ......... 260/397.4

Primary Examiner—Leonard Schenkman
Assistant Examiner—Joseph A. Lipovsky
Attorney, Agent, or Firm—Bierman and Muserlian

[57] ABSTRACT

Novel 17-(formamidosulfonylmethylene)-steroids of the formula

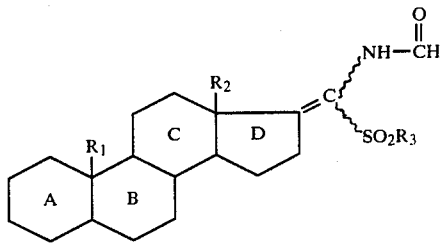

useful as intermediates for the novel 17-(isocyanosulfonylmethylene)-steroids of the formula

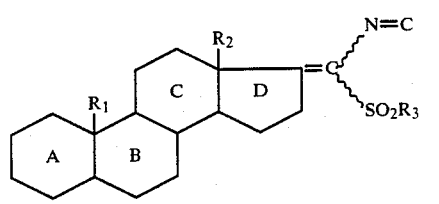

which are useful intermediates for 21-hydroxy-20-keto-$\Delta^{16}$-steroids and 20-keto-$\Delta^{16}$-steroids.

12 Claims, No Drawings

NOVEL 17-SUBSTITUTED STEROIDS

STATE OF THE ART

Steroids are used on a large scale as the active ingredients of many types of pharmaceutical compositions and depending on the substituent pattern of the carbon-skeleton, the steroids can be divided into a number of main classes. An important main class of steroids is formed by the cortico-steroids whose natural representatives are usually produced by the adrenal gland. Corticosteroids are characterized by the presence of a 3-keto group, a $\Delta^4$-double bond, an 11$\beta$-hydroxy group, a 17$\alpha$-hydroxy group and a 17$\beta$-hydroxy-acetyl side chain.

For a long time, corticosteroids were made by chemical degradation of gall acids as cholic acid, desoxycholic acid and glycocholic acid. Afterwards, hecogenin which could be isolated from plants, particularly from numerous Agave species, became an important raw material too. Since the possibility of the introduction of an 11-hydroxy group by microbiological methods, diosgenin which could be isolated from numerous Dioscoreacaea species and stigmasterol, usually isolated from the phytosterol mixture from soya or calabar beans, have become the most important raw material for the preparation of corticosteroids.

Much attention has been given to new, cheaper raw materials for the synthesis of pharmaceutically active steroids. Therefore, the degradation of the abundant soya bean derived sterols, sitosterol and campesterol by microbiological methods into 17-oxo-steroids was extensively investigated and as a result thereof, 17-oxo-steroids are readily available now at low prices which makes these compounds, together with the possibility of the introduction of an 11-hydroxy group by microbiological methods, ideal starting materials for corticosteroid synthesis.

A number of chemical synthesis for the construction of the corticosteroids side chain from 17-oxo-steroids is known. For instance, J. Org. Chem., Vol. 44, p. 1582 (1979) describes a method which uses a sulfenate-sulfoxide rearrangement for the introduction of the 17-(dihydroacetone) side chain. Another route is described in J.C.S. Chem. Comm., 1981, p. 775 in which the reaction of 17-oxo-steroids with ethyl isocyanoacetate is described followed by a number of other reactions, which ultimately result in the dihydroxyacetone side chain of corticosteroids. Other syntheses of the corticosteroid side chain or of compounds which can be used as precursors therefore are described in J.C.S. Chem. Comm., 1981, p. 774, J.C.S. Chem. Comm., 1982, p. 551, Chem. Ber., Vol. 113, p. 1184 (1980), and J. Org. Chem., 1982 p. 2993.

OBJECTS OF THE INVENTION

It is an object of the invention to provide the novel 17-(formamidosulfonylmethylene)-steroids of formula I and a process for their preparation.

It is another object of the invention to provide the novel 17-(isocyanosulfonylmethylene)-steroids of formula II and a process for their preparation.

These and other objects and advantages of the invention will become obvious from the following detailed description.

THE INVENTION

The novel 17-(isocyanosulfonylmethylene)-steroids of the invention have the formula

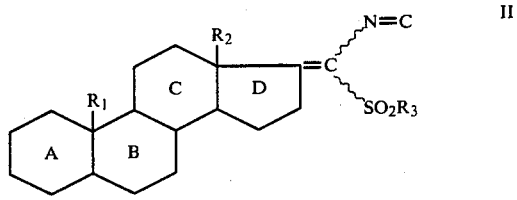

wherein $R_1$ is selected from the group consisting of hydrogen and alkyl of 1 to 4 carbon atoms or may form a double bond in the 1(10), 5(10) or 9(10) position, $R_2$ is selected from the group consisting of hydrogen and alkyl of 1 to 4 carbon atoms, $R_3$ is selected from the group consisting of alkyl of 1 to 10 carbon atoms, dialkylamino of 1 to 8 alkyl carbon atoms, heterocycle of 4 to 8 atoms optionally containing an oxygen atom and aryl optionally substituted with at least one member of the group consisting of halogen and alkyl and alkoxy of 1 to 6 carbon atoms and the A,B,C and D rings may contain at least one double bond and may be optionally substituted with at least one member of the group consisting of hydroxy, amino, oxygen, halogen, alkyl and alkylene and alkoxy of 1 to 6 carbon atoms and alkoxyalkoxy of 2 to 6 carbon atoms and optionally disubstituted with at least one member of the group consisting of epoxy, methylene and alkylenedioxy and alkylenedithio and alkyleneoxythio of 1 to 3 carbon atoms.

Examples of $R_3$ are alkyl of 1 to 10 carbon atoms such as methyl, ethyl, isopropyl, n-butyl and octyl; dialkylamino with alkyls of 1 to 8, preferably 1 to 4 carbon atoms, such as dimethylamino or diethylamino; heterocycle of up to 8 ring atoms optionally containing an oxygen atom such as pyrrolidine and morpholine; and aryl such as phenyl or naphthyl optionally substituted with at least one member of the group consisting of halogen and alkyl and alkoxy of 1 to 6 carbon atoms such as phenyl, p-methoxyphenyl and p-methylphenyl.

When the rings A, B, C and D contain one or more double bonds, the double bonds are preferably present between $C_1$ and $C_2$, $C_3$ and $C_4$, $C_4$ and $C_5$, $C_5$ and $C_6$, $C_6$ and $C_7$, $C_9$ and $C_{10}$, $C_9$ and $C_{11}$ and/or $C_{11}$ and $C_{12}$. More preferably, the double bonds is between $C_4$ and $C_5$ and/or $C_9$ and $C_{11}$. When two or more double bonds are present, the following systems are especially preferred: $C_3-C_4$ and $C_5-C_6$, $C_4-C_5$ and $C_6-C_7$, $C_1-C_2$ and $C_4-C_5$, $C_1-C_2$, $C_3-C_4$ and $C_5-C_{10}$ and $C_1-C_2$, $C_4-C_5$ and $C_6-C_7$. Preferably, there is also a double bond between $C_9$ and $C_{11}$.

When the rings A, B, C and D are substituted with hydroxy, suitable substituents are 3-, 9-, 11-, 12- or 14-hydroxy, preferably a 3- or 9-hydroxy. When the rings A, B, C and D are substituted with an amino, suitable aminos are 3-alkylaminos preferably containing 1-4 carbon atoms, 3-dialkylamino groups wherein the alkyls are the same or different and each alkyl preferably contains 1-4 carbon atoms, or amino groups in which the nitrogen atom together with the alkyls form a heterocyclic ring, preferably containing 1-8 ring atoms which ring optionally may contain an oxygen atom. Particularly preferred are dimethylamino, diethylamino, pyrrolidine and morpholine.

When the rings A, B, C and D are substituted with an oxygen atom, the oxygen atom is preferably present at $C_3$, $C_{11}$ or $C_{12}$. When the rings A, B, C and D are substituted with a halogen, suitable halogens are 6-, 9- or 11-fluorine, chlorine or bromine atoms, preferably 6- or 9-fluorine or chlorine atoms.

When the rings A, B, C and D are substituted by an alkyl, suitable alkyls are 1-, 2-, 6-, 7- or 16-methyl, preferably 1 or 6-methyl. When the rings A, B, C and D are substituted by an alkoxy, suitable alkoxys are 3-, 9-, 11- or 12-alkoxy containing 1-4 carbon atoms, preferably 3-, 9-, or 11-methoxy or ethoxy groups. When the rings A, B, C and D are substituted by an alkoxyalkoxy, suitable groups are 3- or 11-methoxymethoxy, methoxyethoxy or tetrahydropyranyloxy. When the rings A, B, C and D are disubstituted, suitable substituents are epoxy groups at $C_1$ and $C_2$ or $C_9$ and $C_{11}$ or a methylene group attached to $C_1$ and $C_2$ or a 3,3-alkylenedioxy, a 3,3-alkylenedithio or a 3,3-alkyleneoxythio group. The alkylene group preferably contains 2 or 3 carbon atoms.

More particularly, the invention relates to compounds in which $R_1$ and $R_2$ are methyl or in which $R_1$ is absent, which are substituted by halogen, especially fluorine, or hydroxy at $C_9$ and a hydroxy or keto group at $C_{11}$, or containing functional groups such as a double bond or epoxy group between $C_9$ and $C_{11}$, which can be converted by methods known in the art into the groups mentioned before, and which contain a keto group at $C_3$ and double bonds between $C_1$ and $C_2$ and/or $C_4$ and $C_5$, or containing functional groups which can be converted into the keto group and double bonds mentioned before.

The 17-(isocyanosulfonylmethyl)-steroids, are valuable intermediates in the preparation of 21-hydroxy-20-keto-delta$^{16}$-steroids and 20-keto-delta$^{16}$-steroids as described in the applications Serial No. and entitled: "New process for the preparation of 21-hydroxy-20-keto-$\Delta^{16}$-steroids and new intermediate compounds formed in this process" and "New process for the preparation of 20-keto-$\Delta^{16}$-steroids and new intermediate compounds formed in this process" filed on even date herewith, the contents of both applications have to be regarded as included herein. These compounds can be conveted into pharmaceutically active steroids by methods known in the art.

The before-mentioned 21-hydroxy-20-keto-$\Delta^{16}$-steroids are prepared by reaction of a 17-(isocyano-sulfonylmethylene)-steroid with an aldehyde and an alcohol under basic conditions, followed by hydrolysis of the intermediate 17-(2-alkoxy-3-oxazolin-4-yl)-$\Delta^{16}$-steroids. The beforementioned 20-keto-$\Delta^{16}$-steroids are prepared by reaction of a 17-(isocyano-sulfonylmethylene)-steroid with an alkylating agent under basic conditions followed by hydrolysis of the intermediate 20-isocyano-20-sulfonyl-$\Delta^{16}$-steroid.

The invention also relates to a process for the preparation of 17-(isocyano-sulfonylmethylene)-steroids by reacting a 17-oxo-steroid with a sulfonylmethylisocyanide and then dehydrating the resulting formamide to the corresponding isocyanide. Such a process is known. For instance, European patent application No. 7672 discloses the said process applied to numerous ketones. It has now been found that 17-(formamido-sulfonylmethyllene)-steroids and 17-(isocyano-sulfonylmethyl)-steroids can be prepared by the process described in European patent application No. 7672 starting with 17-oxo-steroids.

Therefore the invention also relates to a process for the preparation of 17-(isocyanato-sulfonylmethylene)-steroids by reacting a ketone with a sulfonylmethylisocyanide, followed by dehydration of the resulting formamide, characterized in that the ketone is a 17-oxo-steroid. In this connection, the following is observed. The above mentioned European patent application contains one example (Example 60) in which a steroid is used for the preparation of an $\alpha,\beta$-unsaturated sulphonylmethyl formamide, and also the dehydration of this formamide to the corresponding isocyanide is described (Example 26) but in these examples, the starting material was a 3-oxo-steroid.

However, as the 3-oxo-group of a steroid is more reactive than the 17-oxo group, mainly due to steric reasons, it is not predictable for a man skilled in the art that these reactions also could be performed at the 17-oxo-group, especially because of the known difficulties of reactions of p-methylphenylsulfonylmethyl-isocyanide in other type of reactions with sterically hindered ketones.

In this respect, reactions of p-methylphenylsulfonylmethylisocyanides with 17-oxo-steroids were known already, as appears from, for instance, Tetrahedron, Vol. 31, p. 2151 and 2157. In these publications, the preparation of 17-$\alpha$ and 17-$\beta$-cyano-steroids is described. As a result of the already before mentioned steric hindrance of the 17-oxo-group, the reaction with p-methylphenylsulfonylmethylisocyanide with 17-cyano steroids could only be performed by using drastic reaction conditions. It is generally believed that the above-mentioned $\alpha,\beta$-unsaturated formamides, or more accurately their deprotonated anions, are intermediates in the formation of the cyano compounds.

Using the drastic reaction conditions necessary for the first step in the reaction scheme in view of the steric hindrance of the 17-oxo-group, one would except that the formamides, once formed, would react immediately further into the before mentioned cyano-compounds, and thus, isolation of the $\alpha,\beta$-unsaturated formamides would be impossible. It was therefore surprising that it was still possible to isolate the desired $\alpha,\beta$-unsaturated formamides instead of the cyanides which would be expected. This could be reached mainly by using sufficiently low temperatures, i.e. temperatures below $-20°$ C., preferably at $-40°$ C.

The invention also relates to the intermediate 17-(formamido-sulfonylmethylene)-steroids of the formula

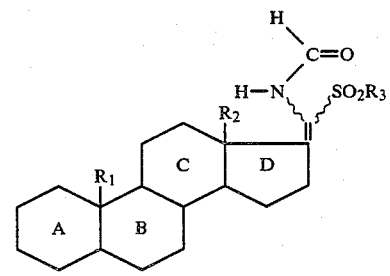

in which the substituents are as defined above.

Furthermore, the invention also relates to a process for the preparation of 17-(formamido-sulfonylmethylene)-steroids by reacting a 17-oxo-steroid with a sulfonylmethyl isocyanide. As the 17-(formamido-sulfonylmethylene)-steroids are intermediates in the preparation of 17-(isocyano-sulfonylmethylene)-steroids, the invention also relates to a process for the preparation of 17-(isocyano-sulfonylmethylene)-steroids, characterized in that a 17-(formamido-sulfonylmethylene)-steroid is dehydrated. It is a further feature of the invention that both steps of the preparation process can be combined into a "one-pot-process".

If necessary to obtain the desired steroids, or to improve the yield, protective groups may be introduced and the protective group may be removed after the first or the second reaction step. The former is recommendable when the protective group affects unfavorably the second reaction step. The presence of a protective group can also be important when the isocyanides of the invention are used as intermediates for the preparation of 21-hydroxy-20-keto-$\Delta^{16}$-steroids or 20-keto-$\Delta^{16}$-steroids as described in the simultaneously filed applications. Therefore, it is not always necessary to remove the protective group, sometimes it is even undesired. For example, methoxy together with a double bond between $C_3$ and $C_4$ or tetrahydropyranyloxy at the 3-position are protective groups for the 3-oxo- or 3-hydroxy group and are preferably kept until their hydrolysis during the last reaction step in the preparation of the said hydroxy-keto-steroids.

Suitable 17-oxo-steroids for the process of the invention are 17-oxo-steroids of the formula

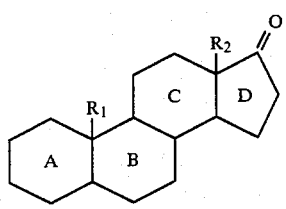

III wherein the steroid is as defined above. Those steroids which contain one or more groups which would interfere during the reaction have to be protected at the relevant positions and this can be done by methods known in the art.

For the reaction of the 17-oxo-steroids with the sulfonylmethylisocyanides, the general reaction conditions can be used as described by Schollkopf et al. Agnew. Chemie. Int. Ed., Vol. 12, p. 407 (1973) and by Van Leusen et al, Recl. Trav. Chim. Pays Bas., Vol. 98, p. 258 (1982). The temperature during the reaction has to be kept below $-20°$ C. Usually the reaction is carried out with a strong alkaline agent in an organic solvent, preferably under an inert gas atmosphere. Examples of useful strong alkaline agents are alkali metal alcoholates such as alkali metal t-butylates and alkali metal ethanolates, alkali metal hydrides, alkali metal amides, alkali metal alkyls and alkali metal aryls in which the alkali metal is generally lithium, sodium or potassium and amines, preferably alkylamines. Potassium t-butoxide is preferably used. The reaction has to be carried out at lower temperatures between $-20°$ and $-80°$ C., preferably between $-30°$ and $-60°$ C., depending on the solvent used too.

The reaction is further preferably carried out in a polar organic solvent such as tetrahydrofuran, dimethylformamide, 1,2-dimethoxyethane, hexamethylphosphortriamide, dioxane, toluene or mixtures thereof. Tetrahydrofuran is preferred. The inert gas atmosphere is preferably a nitrogen or an argon atmosphere.

It will be appreciated that in principle, $R_3$ of the sulfonylmethylisocyanides $R_3-SO_2-CH_2-N\equiv C$ to be used can be any group which does not interfere in the reaction and at least it will be possible to use those classes of sulfonylisocyanides which have been used already for this type of reactions. Examples of these classes are those compounds in which $R_3$ is aryl, alkyl or dialkylamino and whereby optionally one or more substituents can be present as described above.

Suitable sulfonylmethylisocyanides are arylsulfonylmethylisocyanides in which the aryl group is phenyl or naphthyl optionally substituted by at least one member of the group consisting of alkyl and alkoxy. Preferably arylsulfonylmethylisocyanides are phenylsulfonylmethylisocyanides in which the phenyl group is optionally substituted with a halogen, one or more alkyls or an alkoxy. Particularly preferred are phenylsulfonylmethylisocyanide and p-methylphenylsulfonylmethylisocyanide.

Any method for the preparation of the $\alpha,\beta$-unsaturated isocyanides from the corresponding formamides may be used, for example the reaction with phosphoroxy chloride in the presence of an amine. This reaction is preferably carried out at lower temperatures, e.g. between $-50°$ and $25°$ C., preferably between $-30°$ and $-5°$ C. Other dehydrating agents, may however, also be used. Examples thereof are phosgene, thionyl chloride, cyanuryl chloride, alkyl and arylsulfonyl chlorides, a mixture of triphenylphosphine, carbon tetrachloride and triethylamine, 2-chloro-3-ethylbenzoxazolium tetrafluoroborate or phosphorus tri or pentachloride (see Ugi, Isonitril Chemistry, Acad. Press New York, 1971, pages 10 to 16) and diphosgene (see Agnew. Chemie., 89, 2671 (1977).

The dehydration is preferably carried out in the presence of an acid-binding agent such as an amine. Examples of suitable amines are triethylamine, substituted or unsubstituted pyridines, N-methylmorpholine, while other alkaline agents may be used too, such as potassium carbonate, sodium carbonate or potassium t-butoxide. The dehydration is preferably carried out in an inert organic solvent such as di-, tri- or tetra-chloromethane, ethyl acetate, dioxane, tetrahydrofuran, benzene, toluene, xylene, o-dichlorobenzene, acetone, 1,2-dimethoxyethane, bis(2-methoxyethyl)-ether, dimethylformamide or 1,2-dichloroethane or mixtures thereof.

In the following examples there are described several preferred embodiments to illustrate the invention. However, it is to be understood that the invention is not intended to be limited to the specific embodiments. TosMIC indicates tosylmethyl isocyanide (p-methylphenylsulfonylmethyl isocyanide) and the specific rotation was measured using light of sodium D line.

EXAMPLE 1a 3-methoxy-17-(isocyano-p-methylphenylsulfonylmethylene)-$\Delta^{3,5}$-androstadiene 840 mg (7.5 mmol) of potassium t-butoxide were added to 50 ml of dry tetrahydrofuran and the suspension was cooled to $-40°$ C. 1.17 (6 mmol) of TosMiC were added to the suspension at $-40°$ C. and after 10 minutes stirring at this temperature, 1.5 g (5 mmol) of 3-methoxy-$\Delta^{3,5}$-androstadien-17-one were added. The mixture was stirred for two hours at $-40°/-30°$ C., followed by the addition of 615 mg (7.5 mmol) of phosphoric acid at $-35°$ C. After stirring for 10 minutes, 7.5 ml (54 mmol) of triethylamine and 1 ml (11 mmol) of phosphoroxytrichloride were added at $-35°$ C. The reaction mixture was stirred for one hour at $0°$ C. and was poured into a mixture of 250 ml of ice water and 50 ml of sodium chloride. Extraction with $CH_2Cl_2$ and the organic phase was dried over $MgSO_4$ and evaporated under reduced pressure to dryness. The residue was crystallized from methanol to obtain 1.72 g (3.6 mmol, 72%) of $\alpha,\beta$-unsaturated isocyanide melting at 205° C. (dec.); $(\alpha)^{20}$ −85° (c 0.675, $CHCl_3$);

IR (Nujol)

2140 (N≡C), 1655, 1632, 1612 (C═C), 1600 (Ar), 1340 and 1162 ($SO_2$) cm$^{-1}$;

$^1$H NMR ($CDCl_3$)

delta 0.8–3.2 (m), 0.96 (s, 3H), 2.42 (s), 3.5 (s, 3H), 5.0–5.3 (m, 2H), 7.15, 7.33, 7.64, 7.80 (ABq, 4H).

Analysis: $C_{29}H_{30}NO_3S$; molecular weight=477.67. Calculated: %C 72.92; %H 7.39; %N 2.93; %S 6.71. Found: 72.7; 7.4; 2.9; 6.7.

Hydrolysis of 2.36 g (5 mmol) of 3-methoxy-17-(isocyano-p-methylphenylsulfonylmethylen)-$\Delta^{3,5}$ androstadiene into 17-(isocyano-p-methylphenylsulfonylmethylene)-$\Delta^4$-andristene-3-one was performed in a mixture of 20 ml of acetic acid, 35 ml of methylene chloride and 1 ml of water at 25° C. After stirring for two hours, the reaction mixture was poured into water, and was extracted with methylene chloride. After washing with a sodium bicarbonate solution, the organic layer was dried over $MgSO_4$ and evaporated to dryness in vacuum. The 2 g of residue were crystallized from methanol to obtain crystals melting at 170°–175° C. (dec.)

IR (nujol): 2140,2130 (N≡C), 1675 (C═O), 1620 (C═C), 1330,1160 ($SO_2$) cm$^{-1}$. $^1$H MNR ($CDCl_3$): delta 0.6–3.7 (m), 0.98 (s), 1.18 (s), 2.43 (s), 5.65 (s), 7.20, 7.35, 7.65, 7.80(ABq).

EXAMPLE 1b 3-methoxy-17-(formamido-p-methylphenylsulfonylmethylene)-$\Delta^{3,5}$-androstadiene 1.26 g of potassium-t-butoxide were added to 50 ml of tetrahydrofuran whereafter the suspension was cooled to −50° C. 1.17 g of TosMIC were added to the suspension and after 10 minutes of stirring at this temperature, 1.5 g of 3-methoxy-$\Delta^{3,5}$-androstadiene-17-one were added. The mixture was stirred for 2.5 hours at −40°/−55° C., followed by addition of 0.92 g of $H_3PO_3$. The reaction mixture was stirred for 20 minutes, and poured into a mixture of 250 ml of ice water and 50 ml of sodium chloride. The mixture was extracted with $CH_2Cl_2$ and the organic phase was dried over $MgSO_4$, evaporated to dryness in vacuum and the residue was crystallized from hexane-$CH_2Cl_2$ to obtain 1.47 g (59%) of $\alpha,\beta$-3-methoxy-17-(formamido-p-methylphenylsulfonylmethylene)-$\Delta^{3,5}$-androstadiene.

IR ($CHCl_3$): 3396, 3367 (NH), 1699 (C═O), 1654, 1626, 1559 (C═C), 1316, 1141, ($SO_2$) cm$^{-1}$.

MNR ($CDCl_3$): 0.945 (s, 6H), 2.41 (s, 3H); 3.53 (s, 3H), 5.16 (m, 2H), 7.2–8.2 (m, 6H).

EXAMPLE 2

3-methoxy-17-(isocyano-p-methylphenylsulfonylmethylene)-$\Delta^{1,3,5(10)}$-estratriene Using the procedure of Example 1a, 1.42 g (5 mmol) of 3-methoxy-$\Delta^{1,3,5(10)}$-triene-17-one were reacted. The $\alpha,\beta$-unsaturated isocyanide was precipitated from methanol as a gel and the methanol was removed and the gel was dried in vacuum to obtain 1.62 g (70% yield) of 3-methoxy-17-(isocyano-p-methylphenylsulfonylmethylene)-$\Delta^{1,3,5(10)}$-estratriene melting at 82°–86° C. (dec.). $(\alpha)^{20}$ +46° (c 1.00, $CHCl_3$).

IR (Nujol): 2150 (N≡C), 1618, 1620 (Arom+C═C), 1390, 1342, 1162 ($SO_2$) cm$^{-1}$.

$^1$H NMR ($CDCl_3$): delta 1.1–3.2 (m), 2.42 (s, 3H), 3.70, (s,3H), 6.53 (s, 1H), 6.68 (s, 1H), 7.00 (s, 1H), 7.21, 7.34, 7.69, 7.83 (ABq, 4H).

Analysis: $C_{28}H_{31}NO_3S$; molecular weight=461.62. Calculated: %C 72.85; %H 6.77; %N 3.03; %S 6.95. Found: 73.1; 7.2; 2.85.

EXAMPLE 3

17-(isocyano-p-methylphenylsulfonylmethylene)-$\Delta^{1,4}$-androstadiene-3-one Using the procedure of Example 1a, 1.42 g (5 mmol) of $\Delta^{1,4}$-androstadiene-3,17-dione were reacted. After crystallization from methanol at −20° C., the 1.35 g (59%) of isocyanide was obtained as a white solid melting at 181°–183° C. (dec.). $(\alpha)^{20}$ +181° (c 1.00, $CHCl_3$).

IR (Nujol): 2140 (N≡C), 1665 (C═O), 1630, 1610 (C═C), 1600 (Ar), 1380, 1335, 1160 ($SO_2$) cm$^{-1}$.

$^1$H NMR ($CDCl_3$): delta 0.8–3.2 (m), 1.0 (s), 1.21 (s), 2.43 (s), 6.00, 6.04, 6.20, 6.23 (2×d 2H), 6.83, 7.00, (d, 2H), 7.18, 7.33, 7.65, 7.78, (ABq, 4H).

Analysis: $C_{28}H_{31}NO_3S$; molecular weight=461.62. Calculated: %C 72.85; %H 6.77; %N 3.03; %S 6.95. Found: 72.6; 6.8; 3.0; 7.0.

EXAMPLE 4

3-methoxy-17-(isocyano-p-methylphenylsulfonylmethylene)-$\Delta^{3,5,9(11)}$-androstatriene Using the procedure of Example 1a, 1.49 g (5 mmol) of 3-methoxy-$\Delta^{3,5,9(11)}$-androstatriene-17-one were reacted and the raw product was crystallized from 40 ml of methanol to obtain 1.84 g (77% yield) of 3-methoxy-17-(isocyano-p-methylphenylsulfonylmethylene)-$\Delta^{3,5,9(11)}$-androstatriene melting at 162°–167° C. Two further crystallizations from methylene chloride-methanol (1:4) gave a product with a melting point of 172° (dec.). $(\alpha)^{20}$ −109° (c 1.00, $CHCl_3$).

IR (Nujol): 2150 (N≡C), 1660, 1640, 1615 (C═C), 1605 (Ar), 1380, 1345, 1270 ($SO_2$) cm$^{-1}$.

$^1$H NMR ($CDCl_3$): delta 0.8–3.3 (m), 0.90 (s), 1.09 (s), 2.41 (s), 3.50 (s, 3H), 5.0–5.55 (m, 3H), 7.20, 7.35, 7.65, 7.80, (ABq, 4H).

Analysis: $C_{29}H_{33}NO_3S$; molecular weight=475.65 Calculated: %C 73.23; %H 6.99; %N 2.94; %S 6.74. Found: 72.7; 7.0; 3.0; 6.7.

EXAMPLE 5

3-methoxy-17-(isocyano-p-methylphenylsulfonylmethylene)-$\Delta^{3,5}$-androstadiene-11$\beta$-ol 420 g (about 3.75 mmol) of potassium t-butoxide were added to dry tetrahydrofuran under nitrogen and the suspension was cooled to −40° C. Then 585 mg (3 mmol) of TosMIC and 3-methoxy-$\Delta^{3,5}$-androstadiene-11$\beta$-ol-17-one were added thereto. After two hours of stirring at −40°/−35° C., 308 mg (3.75 mmol) of $H_3PO_3$ were added, followed after 10 minutes by 7.5 ml (54 mmol) of triethylamine and 1 ml (11 mmol) of $POCl_3$. $POCl_3$ was added over a period of about five minutes so that the temperature remained below −30° C. After two hours of stirring at −30°/−35° C., the reaction mixture was poured into a mixture of 150 ml of water and 50 ml of sodium chloride followed by extraction successively with 60,30 and 30 ml of $CH_2Cl_2$. After drying, the organic phase was filtered through $Al_2O_3$ (act. II-III) and evaporated to obtain an oil. Addition of 20 ml of methanol yielded crystals after cooling at $-20°$ C. Drying over sodium chloride at 0.2 mm Hg yielded 940 mg (76%) of 3-methoxy-17-(isocyano-p-methylphenylsulfonylmethylene)-$\Delta^{3,5}$-androstadiene-11$\beta$-ol melting at 180° C. (dec.). After two further crystallizations from 10 ml of $CH_2Cl_2/CH_3OH$ (1:5), the resulting substance had a melting point of 188° C. (dec.). $(\alpha)^{20} -81°$ (c 1.00, $CHCl_3$).

IR (Nujol): 3650 (OH), 2150 (N≡C), 1655, 1630, 1615, 1598 (C=C+Ar), 1340, 1165 cm$^{-1}$ ($SO_2$).

$^1$H NMR ($CDCl_3$): delta 0.8–3.8 (m), 1.18 (s), 2.42 (s), 3.5 (s), 4.25–4.55 (m, 1H), 5.03 (s, 2H), 7.19, 7.33, 7.66, 7.79 (ABq, 4H).

Analysis: $C_{29}H_{35}NO_4S$; molecular weight=493.667. Calculated: %C 70.56; %H 7.15; %N 2.84; %S 6.49. Found: 70.1; 7.2; 2.7; 6.5.

EXAMPLE 6

3-methoxy-9$\alpha$-fluoro-17-(isocyano-p-methylphenylsulfonylmethylene)-$\Delta^{3,5}$-androstadiene-11$\beta$-ol 835 mg (2.5 mmol) of 3-methoxy-9$\alpha$-fluoro-11$\beta$-hydroxy-$\Delta^{3,5}$-androstadien-17-one were reacted as described in Example 5 and the crude isocyano compound was crystallized from 15 ml of methanol and washed with two portions of 5 ml of cold methanol. After drying, 810 mg (63.5%) of 3-methoxy-9$\alpha$-fluoro-17-(isocyano-p-methylphenylsulfonylmethylene)-$\Delta^{3,5}$-androstadiene-11$\beta$-ol melting at 180° C. (dec.). $(\alpha)^{20} -87°$ (c 1.00, $CHCl_3$) were obtained.

IR (Nujol): 3580 (OH), 2170 (N≡C), 1662, 1640, 1620, 1605 (C=C+Ar), 1345, 1165 ($SO_2$) cm$^{-1}$.

$^1$H NMR ($CDCl_3$): delta 0.8–3.3 (m), 1.17 (s), 1.24 (s), 2.42 (s), 3.50 (s, 3H), 4.05–4.60 (m, 1H), 5.10 (s, br, 2H), 7.21, 7.32, 7.67, 7.78 (ABq, 4H).

EXAMPLE 7

3-methoxy-17-(isocyano-p-methylphenylsulfonylmethylene)-$\Delta^{3,5}$-androstadiene-11-one 785 mg (2.5 mmol) of 3-methoxy-$\Delta^{3,5}$-androstadiene-11,17-dione was treated as described in Example 1a, however using half the quantities mentioned therein. After crystallization from 10 ml of methanol, 875 mg (71%) of 3-methoxy-17-(isocyano-p-methylphenylsulfonylmethylene)-$\Delta^{3,5}$-androstadiene-11-one melting at 195°–205° C. (dec.) were obtained. Further purification by two crystallizations from $CH_2Cl_2$/methanol yielded a substance melting at about 220° (dec.) and an $(\alpha)^{20}$ of $-86.5°$ (c 1.00, $CHCl_3$).

IR (Nujol): 2150 (N≡C), 1705 (C=O), 1655, 1635, 1615 (C=C), 1595 (Ar), 1340, 1170 ($SO_2$) cm$^{-1}$.

$^1$H NMR ($CDCl_3$): delta 0.7–3.8 (m), 0.92 (s) 1.12 (s), 2.45 (s), 3.50 (s), 4.85–5.30 (m, 2H), 7.19, 7.33, 7.62, 7.77 (ABq, 4H).

Analysis: $C_{29}H_{33}NO_4S$; molecular weight=491.65. Calculated: %C 70.85; %H 6.77; %N 2.85; %S 6.52. Found: 70.9; 6.8; 2.7; 6.6.

EXAMPLE 8a

1$\alpha$,2$\alpha$-methylene-6-chloro-17-(formamido-p-methylphenylsulfonylmethylene)-$\Delta^{4,6}$-androstadiene-3-one 412 mg (3.68 mmol) of potassium t-butoxide were added to 30 ml of dry THF and the suspension was cooled to $-40°$ C. under nitrogen. Then 575 mg (2.94 mmol) of TosMIC were added and after dissolution, the temperature was lowered to $-75°$ C., followed by the addition of 810 mg (2.45 mmol) of 6-$\alpha$-chloro-1$\alpha$,2$\alpha$-methylene-$\Delta^{4,6}$-androstadiene-3,17-dione. After 5 hours of stirring, TosMIC was no longer present and 1$\alpha$,2$\alpha$-methylene-6-chloro-17-(formamido-p-methylphenylsulfonylmethylene)-$\Delta^{4,6}$-androstadiene-3-one was isolated and it had a melting point of 259°–260° C.

$^1$H NMR ($CDCl_3$): delta 0.6–0.9 (m, cyclopropyl), 1.002 (s, 3H), 1.204 (s, 3H), 2.46 (s, 3H) 6.3 (m, 2H) 7.3–8.4 (m, 6H).

EXAMPLE 8b

1$\alpha$,2$\alpha$-methylene-6-chloro-17-(isocyano-p-methylphenylsulfonylmethylene)-$\Delta^{4,6}$-androstadiene-3-one 300 mg of the formamide prepared in Example 8a were dissolved in 6 ml of tetrahydrofuran and cooled to $-20°$ C. under nitrogen. Then 0.8 ml of triethylamine and 0.11 ml of $POCl_3$ were added, following by stirring for a half an hour at $-20°$ C. The isocyanide was isolated and purified according to Example 1a to obtain 1$\alpha$,2$\alpha$-methylene-6-chloro-17-(isocyano-p-methylphenylsulfonylmethylene)-$\Delta^{4,6}$-androstadiene-3-one melting at 144°–151° C. (browning at 118° C.).

IR ($CHCl_3$): 2210 (N≡C), 1660 (C=O), 1615, 1601 (C=C), 1345, 1160 ($SO_2$) cm$^{-1}$.

$^1$H NMR ($CDCl_3$): delta 0.6–0.9 (m, cyclopropyl), 1.025 (s, 3H), 1.200 (s, 3H), 2.43 (s, 3H), 6.16 (m, 2H), 7.31–7.77 (m, 4H).

EXAMPLE 9

3,3-ethylenedithio-17-(isocyano-p-methylphenylsulfonylmethylene)-$\Delta^4$-androstene 464 mg (4.41 mmol) of potassium t-butoxide were added to 25 ml of dry THF and the mixture was cooled to $-60°$ C. under nitrogen. Then 0.659 mg (3.34 mmol) of TosMIC were added and after 10 minutes, a solution of 1 g (2.76 mmol) of 3,3-ethylenedithio-$\Delta^4$-androsten-17-one in 5 ml of THF was added followed by another 5 ml of THF. After two hours of stirring at $-60°/-30°$ C., 0.24 ml (4.2 mmol) of acetic acid was added at $-40°$ C. After 10 minutes, 4.14 ml of triethylamine and 0.55 ml of $POCl_3$ were added and the mixture was stirred for one hour with addition of dehydrating agents. The temperature rose to $-10°$ C. and the mixture was stirred in a bath of 0° C. To complete the dehydration, the same quantities of triethylamine and $POCl_3$ were again added and the mixture was again stirred for an hour. Then, water was added and the aqueous layer was extracted three times with $CH_2Cl_2$. The collected $CH_2Cl_2$ solutions were dried over $MgSO_4$, filtered and evaporated to dryness to obtain an oil. Crystallization from 20 ml of methanol yielded 0.85 g (yield 57%) of 3,3-ethylenedithio-17-(isocyano-p-methylphenylsulfonylmethylene)-$\Delta^4$-androstene melting at 213°–216° C. (dec.).

IR ($CHCl_3$): 2107 (N≡C), 1608, 1600 (C=C), 1337, 1155 ($SO_2$) cm$^{-1}$.

$^1$H NMR ($CDCl_3$): delta 1.03 (s, 3H), 1.10 (s, 3H), 2.45 (s, 3H), 3.30 (m, 4H), 5.50 (s, 1H) 7.2–7.95 (ABq, 4H).

EXAMPLE 10

3,3-ethylenedioxy-17-(isocyano-p-methylphenylsulfonylmethylene)-$\Delta^5$-androstene About 7.5 mmol of potassium-t-butoxide were added under nitrogen to 50 ml of tetrahydrofuran and the mixture was cooled to $-40°$ C. Then, 1.17 g (6 mmol) of TosMIC were added thereto and after dissolution of 1.65 g (5 mmol) of 3,3-ethylenedioxy-Δ5-androstene-17-one were added. The reaction mixture was stirred at −30°/−40° C. for two hours and though the TosMIC was completely used, the conversion of the steroid was not complete. Complete conversion was obtained by adding twice a further portion of 200 mg of TosMIC. Then 615 ml (7.5 mmol) of H$_3$PO$_3$ were added after about 20 minutes followed by addition of 7.5 ml (54 mmol) of triethylamine and 1 ml (11 mmol) of POCl$_3$. After stirring for one hour in a bath of 0° C. and storing over night in a cool box, the reaction mixture was poured into 300 ml of a cold 10% solution of NaCl and was extracted with CH$_2$Cl$_2$ (one time with 100 ml, then three times with 40 ml). The combined extracts were washed with a 10% NaCl-solution and dried over MgSO$_4$. After evaporation, a semi-solid residue remained which yielded after crystallization from methanol and a trace of pyridine 2.07 g (89%) of 3,3-ethylene-17-(isocyano-p-methylphenylsulfonylmethylene)-Δ5-androstene melting at 183°–186° C. (dec.).

IR (CHCl$_3$): 2105 (N≡C), 1569, 1332, 1150 (SO$_2$) cm$^{-1}$.

$^1$H NMR (CDCl$_3$): delta 0.95 (s, 3H), 1.03 (s, 3H), 2.47 (s, 3H), 3.93 (s, 4H), 5.36 (m, H), 7.40, 7.88 (ABq, 4H).

EXAMPLE 11

3β-(2'-tetrahydropyranyloxy)-17-(isocyano-p-methylphenylsulfonylmethylene)-Δ5-androstene Using the procedure of Example 1b, 3β-(2-'tetrahydropyranyloxy)-Δ5-androsten-17-one was reacted with TosMIC to obtain 3β-(2'-tetrahydropyranyloxy)-17-(isocyano-p-methylphenylsulfonylmethylene)-Δ5-androstene.

$^1$H NMR formamide (CDCl$_3$): delta, 0.887 (s,3H), 0.977 (s, 3H), 2.41 (s, 3H) 3.3–4.1 (m, 2H), 4.68 (m, 1H) 5.30 (m, 1H) 7.2–8.2 (m, 6H). The 300 mg (0.53 mmol) of said compound were dissolved in 6 ml of THF and cooled to −20° C. under dry nitrogen. While stirring, 0.8 ml of triethylamine and 0.11 ml of POCl$_3$ were added. After 30 minutes, the reaction was completed and the reaction mixture was poured into an aqueous 50% NaOH solution cooled in ice and was extracted with CH$_2$Cl$_2$ (one portion of 25 ml, 3 portions of 10 ml). The collected CH$_2$Cl$_2$ extracts were washed with 10% NaCl solution and dried over MgSO$_4$. After filtration, the solvent was evaporated and dried under vacuum to obtain 283 mg of 3β-(2'-tetrahydropyranyloxy)-17-(isocyano-p-methylphenylsulfonylmethylene)-Δ5-androstene melting at 146°–152° C. (browning at 137° C.).

IR (CHCl$_3$): 2106 (N≡C), 1336, 1153 (SO$_2$), 1050 (—COC—)cm$^{-1}$.

$^1$H (NMR (CDCl$_3$): 0.947 (s, 3H), 1.007 (s, 3H), 2.45 (s, 3H), 3.2–4.1 (m, 2H), 4.67 (m, 1H), 5.30 (m, 1H), 7.37–7.82 (ABq 4H).

EXAMPLE 12

1α-methyl-3-methoxy-17-(isocyano-p-methylphenylsulfonylmethylene)-Δ$^{3,5}$-androstadiene Using the procedure of Example 10 1.57 g (5 mmol) of 1α-methyl-3-methoxy-Δ$^{3,5}$-androstadiene-17-one were reacted and after crystallization from methanol at −20° C. 1.33 g (54% yield) of 1α-methyl-3-methoxy-17-(isocyano-p-methylphenylsulfonylmethylene)-Δ$^{3,5}$-androstadiene melting at 157°–171° C. were obtained.

IR (CHCl$_3$): 2108 (N≡C), 1338, 1156 (SO$_2$) cm$^{-1}$.

NMR (CDCl$_3$): delta 0.75 (d, 3H), 0.970 (s, 3H), 1.013 (s, 3H), 2.46 (s, 3H), 3.55 (s, 3H), 5.10 (m, 1H), 5.34 (m, 1H), 7.42–7.90 (ABq, 4H).

EXAMPLE 13

3-methoxy-11α-hydroxy-17-(isocyano-p-methylphenylsulfonylmethylene-Δ$^{3,5}$-androstadiene 160 mg (1.5 mmol) of potassium-t-butoxide were suspended in 12 ml of tetrahydrofuran and the mixture was cooled to −60° C. 234 mg (1.2 mmol) of TosMIC were added, followed after 10 minutes by 316 mg (1.2 mmol) of 3-methoxy-11β-hydroxy-Δ$^{3,5}$-androstadien-17-one. The clear solution was stirred for two hours at −50° C., followed by addition of 3 ml of triethylamine and 0.4 ml of POCl$_3$. The reaction mixture was stirred for 40 minutes at −40°/−50° C. and was poured into a mixture of water and sodium chloride. After extraction with methylene chloride at pH 7, the organic layer was dried and evaporated to dryness. The residue was crystallized from methanol to obtain 260 mg (52% yield) of 3-methoxy-11β-hydroxy-17-(isocyano-p-methylphenylsulfonylmethylene-Δ$^{3,5}$-androstadiene melting at 235° C. (dec.).

$^1$H NMR (CDCl$_3$): 0.98 (s, 3H), 1.10 (s, 3H), 1.49 (s, 1H), 2.47 (s, 3H), 3.55 (s, 3H), 4.07 (m, 1H), 5.10 (s, 1H), 5.22 (m, 1H), 7.36–7.82 (m, 4H).

IR (CHCl$_3$): 3596 (OH), 2100 (N≡C), 1655, 1630, 1610, 1594 (C═C), 1336, 1155 (SO$_2$) cm$^{-1}$.

EXAMPLE 14

3-(N-morpholino)-17-(isocyano-p-methylphenylsulfonylmethylene)-Δ$^{3,5}$-androstadiene Using the procedure of Example 13, 1.78 g (5 mmol) of 3-(N-morpholino)-Δ$^{3,5}$-androstadiene-17-one were reacted to obtain a 52% yield of 3-(N-morpholino)-17-(isocyano-p-methylphenylsulfonylmethylene)-Δ$^{3,5}$-androstadiene melting at 154°–156° C.

$^1$H NMR (CDCl$_3$): 0.97 (s, 2×3H), 2.45 (s, 3H), 2.85–3.10 (m, 4H), 3.6–3.8 (m, 4H), 5.14 (d, 2H), 7.25, 7.41, 7.73, 7.88 (ABq, 4H).

IR (CHCl$_3$): 2105 (N≡C), 1600 (C═C) cm$^{-1}$, 1337, 1150 (SO$_2$) cm$^{-1}$.

EXAMPLE 15

3-methoxy-17-(isocyano-p-methylphenylsulfonylmethylene)-19-nor-Δ$^{3,5}$-androstadiene Using the procedure of Example 13, 725 mg (2.5 mmol) of 3-methoxy-19-nor-Δ$^{3,5}$-androstadiene-17-one were reacted to obtain 671 mg (55% yield) of 3-methoxy-17-(isocyano-p-methylphenylsulfonylmethylene)-19-nor-Δ$^{3,5}$-androstadiene melting at 163°–168° C.

$^1$H NMR (CDCl$_3$+DMSO): 1.0–3.2 (m), 0.97 (s, 3H), 2.47 (s, 3H), 3.55 (s, 3H), 5.22 (m, 2H), 7.30, 7.44, 7.74, 7.88, (ABq, 4H).

IR (CHCl$_3$): 2105 (N≡C), 1334, 1150 (SO$_2$) cm$^{-1}$.

EXAMPLE 16

3-methoxy-6-chloro-17-(isocyano-p-methylphenylsulfonylmethylene-Δ$^{3,5}$-androstadiene Using the procedure of Example 13, 1.65 g of 3-methoxy-6-chloro-Δ$^{3,5}$-androstadien-17-one were reacted to obtain 1.6 g (56% yield) of 3-methoxy-6-chloro-17-(isocyano-p-methylphenylsulfonylmethylene-Δ$^{3,5}$-androstadiene melting at 180°–181° C.

1H NMR (CDCl₃): 0.997 (s, 6H), 2.46 (s, 3H), 3.61 (s, 3H), 5.60 (s, 1H), 7.34–7.82 (ABq, 4H).
IR (CHCl₃): 2106 (N≡C), 1645, 1618, 1598 (C=C).

EXAMPLE 17

3β-methoxymethoxy-17-(isocyano-p-methylphenylsulfonylmethylene)-Δ⁵-androstadiene Using the procedure of Example 13, 1.68 g (5 mmol) of 3β-methoxymethoxy-Δ⁵-androstadien-17-one were reacted to obtain 0.78 of 3β-methoxymethoxy-17-(isocyano-p-methylphenylsulfonylmethylene)-Δ⁵-androstadiene melting at 89°–90° C.

¹H NMR (CDCl₃): 0.95 (s, 3H), 1.01 (s, 3H), 2.45 (s, 3H), 3.34 (s, 3H+1H), 4.65 (s, 2H), 5.30 (s, 1H), 7.25, 7.40, 7.72, 7.86 (ABq, 4H).
IR (CHCl₃): 2106 (N≡C), 1335, 1147 (SO₂), 1597 (C=C), 1035 cm⁻¹.

EXAMPLE 18

3-isobutoxy-17-(isocyano-p-methylphenylsulfonylmethylene)-Δ³,⁵-androstadiene

Using the procedure of Example 1a, 1.17 g (5 mmol) of 3-isobutoxy-Δ³,⁵-androstadiene-17-one were reacted to obtain 1.63 g of 3-isobutoxy-17-(isocyano-p-methylphenylsulfonylmethyl)-Δ³,⁵-androstadiene.

¹H NMR (CDCl₃): delta 0.96 (d, 6H), 0.976 (s, 6H), 2.47 (s, 3H), 3.47 (d, 2H), 5.10 (s, 1H), 5.18 (tr, 1H), 7.39, 7.81 (2×d 4H).
IR (Nujol): 2105 (N≡C), 1647, 1622 (C=C), 1331, 1148 (SO₂).

EXAMPLE 19

3-methoxy-17-(isocyano-p-methylphenylsulfonylmethylene)-Δ³,⁵-androstadiene-9α-ol Using the procedure of Example 1a, 1.3 g (4.1 mmol) of 3-methoxy-Δ³,⁵-androstadiene-9α-ol-17-one were reacted to obtain 1.33 g (54% yield) of 3-methoxy-17-(isocyano-p-methylphenylsulfonylmethylene)-Δ³,⁵-androstadiene-9α-ol melting at 195°–197° C.

¹H NMR (CDCl₃): 0.97 (s, 3H), 1.087 (s, 3H), 2.48 (s, 3H), 2.09–3.16 (m, 2H), 3.58 (s, 3H), 5.16 (s, 1H), 5.28 (m, 1H), 7.39–7.89 (ABq, 4H).
IR (CHCl₃): 3560, 3620 (OH), 2109 (N≡C), 1651, 1669 (C=C), 1158, 1349 (SO₂).

EXAMPLE 20a 3-methoxy-17-(formamido-t-butylsulfonylmethylene)-Δ³,⁵-androstadiene 443 mg (2.75 mmol) of t-butylsulfonylmethylisocyanide were dissolved in tetrahydrofuran and the solution was cooled to −80° C. 1.75 ml (1.6N) of n-butyl lithium were added and after 5 minutes, 0.28 ml (3 mmol) of tert.-butanol were added followed by 0.75 g (2.5 mmol) of 3-methoxy-Δ³,⁵-androstadiene-17-one. The temperature was raised to −40° C. and the mixture was stirred for four hours. 0.5 g of potassium t-butoxide was added, and the mixture was stirred for an additional period of 30 minutes. The reaction mixture was poured into ice-water containing 20 g/l of ammonium chloride. The mixture was extracted with methylene chloride and the organic phase was dried and evaporated to dryness in vacuo to obtain 1.05 g (91%) of 3-methoxy-17-(formamido-t-butylsulfonylmethylene)-Δ³,⁵-androstadiene as a white solid.

IR (Nujol): 3200 (NH), 1700 (C=O), 1655, 1635 (C=C).

¹H NMR (CDCl₃): delta 0.8–3.3 (m), 0.99 (s), 1.18 (s), 1.40 (s), 3.57 (s, 2H), 5.05–5.35 (m, 2H), 7.96, 8.18, 8.66, 8.85 (AB, 2H).

EXAMPLE 20b 3-methoxy-17-(isocyano-t-butylsulfonylmethylene)-Δ³,⁵-androstadiene 1.05 g of the formamide prepared in Example 20a was dissolved in 35 ml of tetrahydrofuran and the mixture was cooled to −5° C. under nitrogen. 3.5 ml of triethylamine and 0.46 ml of POCl₃ were added followed by stirring for 90 minutes at −5° C. The isocyanide was isolated and purified as in Example 1a to obtain 0.82 g (74% yield) calculated on 17-oxo-steroid of 3-methoxy-17-(isocyano-t-butylsulfonylmethylene)-Δ³,⁵-androstadiene melting at 191°–193° C. (dec.). Crystallization from methanol yielded the pure compound melting at 195°–197° C. (dec.), (α)²⁰ −103° (c 1.00, CHCl₃).

IR (Nujol): 2140 (N≡C), 1655, 1635, 1610 cm⁻¹ (C=C).

¹H NMR (CDCl₃): delta 0.8–3.2 (m), 1.00 (s), 1.09 (s), 1.48 (s), 3.57 (s, 3H), 5.05–5.40 (m, 2H).

EXAMPLE 21

3-methoxy-17-(isocyano-methylsulfonylmethylene)-Δ³,⁵-androstadiene

Using the procedure of Example 1a, 625 mg (2.1 mmol) and 298 mg (2.5 mmol) of methylsulfonylmethylisocyanide were reacted to obtain 700 mg (84% yield) of 3-methoxy-17-(isocyano-methylsulfonylmethylene)-Δ³,⁵-androstadiene melting at 198° C. (dec.), (α)²⁰ −111° (c 1.00, CHCl₃).

IR (Nujol): 2140 (N≡C), 1655, 1630, 1615 (C=C), 1330, 1155, 1145 (SO₂).

¹H NMR (CDCl₃): delta 0.8–3.3 (m), 1.0 (s, 3H), 1.08 (s, 3H), 3.06 (s, 3H), 3.56 (s, 3H), 5.1–5.4 (m, 2H).

Analysis: C₂₃H₃₁NO₃S; molecular weight=410.568
Calculated: %C 68.79; %H 7.78; %N 3.49; %S 7.98.
Found: 68.7; 7.9; 3.5; 7.8.

EXAMPLE 22

3-methoxy-17-(isocyano-n-decylsulfonylmethylene)-Δ³,⁵-androstadiene

Using the procedure of Example 1a, 1.5 g (5 mmol) of 3-methoxy-Δ³,⁵-androstadiene and 1.47 g (6 mmol) of n-decylsulfonylmethylisocyanide were reacted and the oil obtained was mixed with methanol, cooled to −20° C., and the white solid, thus obtained was filtered off, and dried to obtain 2.11 g (74% yield) of 3-methoxy-17-(isocyano-n-decylsulfonylmethylene)-Δ³,⁵-androstadiene melting at 110°–113° C.

IR (Nujol): 2130 (N≡C), 1655, 1630, 1615 (C=C), 1335, 1170, 1155, 1140 (SO₂).

¹H NMR (CDCl₃): delta 0.6–3.3 (m), 0.99 (s), 1.06 (s), 1.29 (s), 3.55 (s, 3H), 5.0–5.3 (m, 2H).

EXAMPLE 23

3-methoxy-17-(formamido-pentamethylphenylsulfonylmethylene)-Δ³,⁵-androstadiene 3-methoxy-17-(formamido-pentamethylphenylsulfonylmethylene)-Δ³,⁵-androstadiene was prepared according to the process described in Example 1a and was obtained in a low yield.

EXAMPLE 24

3-methoxy-17-(isocyano-p-methoxyphenylsulfonylmethylene)-$\Delta^{3,5}$-androstadiene Using the procedure of Example 1a, 1.5 g (5 mmol) of 3-methoxy-$\Delta^{3,5}$-androstadiene and 1.279 (6 mmol) of p-methoxyphenylsulfonylmethylisocyanide are reacted to obtain 2.20 g (89% yield) of 3-methoxy-17-(isocyano-p-methoxyphenylsulfonylmethylene)-$\Delta^{3,5}$-androstadiene melting at 155°–160° C. (dec.).

IR (Nujol): 2150 (N≡C), 1660, 1635, 1600 (C=C), 1335, 1155 ($SO_2$).

$^1$H NMR (CDCl$_3$): delta 0.80–3.30 (m), 0.97 (s), 3.56 (s, 3H), 3.88 (s, 3H), 5.05–5.37 (m, 2H), 6.95, 7.10, 7.80, 7.96 (AB, 4H).

EXAMPLE 25

3-methoxy-17-(isocyano-phenylsulfonylmethylene)-$\Delta^{3,5}$-androstadiene

Using the procedure of Example 1a, 1.5 g (5 mmol) of 3-methoxy-$\Delta^{3,5}$-androstadiene and 1.09 g (6 mmol) of phenylsulfonylmethylisocyanide were reacted to obtain 1.55 g (67% yield) of 3-methoxy-17-(isocyano-phenylsulfonylmethylene)-$\Delta^{3,5}$-androstadiene melting at 150°–155° C.

IR (Nujol): 2145 (N≡C), 1655, 1630, 1605 (C=C), 1335, 1170 ($SO_2$).

$^1$H NMR: delta 0.77–3.22 (m), 0.95 (s), 3.49 (s, 3H), 4.93–5.28 (m, 2H), 7.28–7.98 (m, 5H).

EXAMPLE 26a 3-methoxy-17-(formamido-p-chlorophenylsulfonylmethylene)-$\Delta^{3,5}$-androstadiene Using the procedure of Example 20a, 1.35 g (4.5 mmol) of 3-methoxy-$\Delta^{3,5}$-androstadiene and 1.08 g (5 mmol) of p-chlorophenylsulfonylmethylisocyanide were reacted to obtain 2.30 (99% yield) of 3-methoxy-17-(formamido-p-chlorophenylsulfonylmethylene)-$\Delta^{3,5}$-androstadiene.

IR (Nujol): 1700 (C=O), 1660, 1635, 1590 (C=C), 1325, 1150 ($SO_2$).

$^1$H NMR (CDCl$_3$): delta 0.55–2.98 (m), 0.80 (s), 3.21 (s, 3H), 4.50–4.87 (m, 2H), 6.50–7.50 (m, 6H).

EXAMPLE 26b 3-methoxy-17-(isocyano-p-chlorophenylsulfonylmethylene)-$\Delta^{3,5}$-androstadiene Using the procedure of Example 20b, 2.30 g of formamide were reacted to obtain 1.60 g (71% yield) of 3-methoxy-17-(isocyano-p-chlorophenylsulfonylmethylene)-$\Delta^{3,5}$-androstadiene melting at 144°–147° C. (dec.).

IR (Nujol): 2155 (N≡C), 1660, 1635, 1615, 1585 (C=C), 1350, 1165, ($SO_2$), 770 (C—Cl).

$^1$H NMR (CDCl$_3$): delta 0.63–3.20 (m), 0.96 (s), 3.47 (s, 3H), 4.87–5.23 (m, 2H), 7.27, 7.40, 7.62, 7.76 (AB, 4H).

EXAMPLE 27

3-methoxy-11$\beta$-hydroxy-17-(isocyano-p-methoxyphenylsulfonylmethylene)-$\Delta^{3,5}$-androstadiene Using the procedure of Example 5, 2.5 mmol of steroid and 3 mmol of isocyanide were reacted to obtain 1.09 g (85% yield) of 3-methoxy-11$\beta$-hydroxy-17-(isocyano-p-methoxyphenylsulfonylmethylene)-$\Delta^{3,5}$-androstadiene melting at 169°–172° C. (dec.).

IR (Nujol): 3590 (OH), 2125 (N≡C), 1655, 1635, 1590 (C=C), 1325, 1155 ($SO_2$).

$^1$H MNR (CDCl$_3$): delta 0.81–3.30 (m), 1.22 (s), 3.56 (s, 3H), 3.88 (s, 3H), 4.33–4.63 (m, 1H), 5.08 (s, 2H), 7.08, 7.25, 7.78, 7.94 (AB, 4H).

EXAMPLE 28

17-(isocyano-p-methoxyphenylsulfonylmethylene)-$\Delta^{1,4}$-androstadiene-3-one Using the procedure of Example 3, 2.5 mmol of steroid and 3 mol of isocyanide were reacted to obtain 1.00 g (84% yield) of 17-(isocyano-p-methoxyphenylsulfonylmethylene)-$\Delta^{1,4}$-androstadiene-3-one melting at 185°–187° C.

IR (Nujol): 2145 (N≡C), 1660 (C=O), 1620, 1595, (C=C), 1340, 1150 ($SO_2$).

$^1$H NMR (CDCl$_3$): delta 0.78–3.27 (m), 1.02 (s), 1.25 (s), 3.89 (s, 3H), 6.09, 6.11, 6.29, 6.32 (2×d, 2H), 6.97, 7.12, 7.80, 7.97 (AB+d, 5H).

EXAMPLE 29

17-(isocyano-p-methylphenylsulfonylmethylene)-$\Delta^5$-androstene-3-ol

Using the procedure of Example 5, 2.5 mmol of steroid and 3 mmol of isocyanide were reacted to obtain 130 mg (11% yield) of 17-(isocyano-p-methylphenylsulfonylmethylene)-$\Delta^5$-androstene-3-ol melting at 120° C. (dec.).

IR (Nujol): 3500 (OH), 2170 (N≡C), 1610 (C=C), 1145, 1360 ($SO_2$).

$^1$H NMR (CDCl$_3$): delta 0.5–3.8 (m), 0.96 (s), 1.03 (s), 2.47 (s), 3.9–4.6 (m, 1H), 5.25–5.60 (m, 2H), 7.32, 7.46, 7.79, 7.93 (AB, 4H).

EXAMPLE 30a 17-(formamido-p-methylphenylsulfonylmethylene)-$\Delta^4$-androstene-3-one 672 mg (6 mmol) of potassium t-butoxide were added to 40 ml of dry tetrahydrofuran whereafter the suspension was cooled to $-80°$ C. 936 mg (3.8 mmol) of TosMIC were added to the suspension at $-80°$ C. and after 10 minutes, 1.36 g of 3-(1$^1$-pyrrolidyl)-$\Delta^{3,5}$-androstadiene-17-one were added. The mixture was stirred for 5 hours at $-40°$ C. and 2.5 hours at $-35°$ C. and 0.34 ml of acetic acid was added followed by 1.2 g of sodium acetate, 1.2 ml of acetic acid and 6 ml of water. After 45 minutes, the reaction mixture was poured into water and the mixture was extracted with methylene chloride. After drying the organic phase over MgSO$_4$, the solvent was evaporated in vacuo. Chromatography of the residue over alumina oxide (toluene, acetone 9:1) yielded of 0.8 g of 17-(formamido-p-methylphenylsulfonylmethylene)-$\Delta^4$-androstene-3-one melting at 242°–245° C. (dec.).

IR (CHCl$_3$): 3395, 3370 (NH), 1700 (C=O), 1663 (C=O), 1320, 1140 ($SO_2$).

$^1$H NMR (CDCl$_3$): delta 0.93, (s, 3H), 1.15 (s, 3H), 2.42 (s, 3H), 5.75 (8 s, 1H), 7.2–8.3 (m).

EXAMPLE 30b 17-(isocyano-p-methylsulfonylmethylene-$\Delta^4$-androstene-3-one 400 mg of 17-(isocyano-p-methylsulfonylmethylene-$\Delta^4$-androstene-3-one were prepared by the process described in Example 8b starting from 600 mg of the formamide prepared in Example 30a and its physical properties were as described in Example 1a.

Various modifications of the compounds and process of the invention may be made without departing from the spirit or scope thereof and it is to be understood that the invention is intended to be limited only as defined in the appended claims.

What we claim is:

1. A compound of the formula

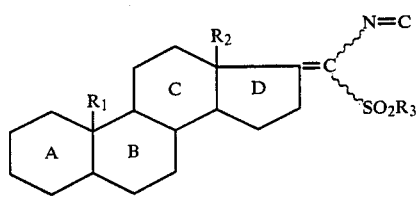

wherein $R_1$ is selected from the group consisting of hydrogen and alkyl of 1 to 4 carbon atoms or may form a double bond in the 1(10), 5(10) or 9(10) position, $R_2$ is selected from the group consisting of hydrogen and alkyl of 1 to 4 carbon atoms, $R_3$ is selected from the group consisting of alkyl of 1 to 10 carbon atoms, dialkylamino of 1 to 8 alkyl carbon atoms, heterocycle of 4 to 8 atoms optionally containing an oxygen atom and aryl optionally substituted with at least one member of the group consisting of halogen and alkyl and alkoxy of 1 to 6 carbon atoms and the A,B, C and D rings may contain at least one double bond and may be optionally substituted with at least one member of the group consisting of hydroxy, amino, oxygen, halogen, alkyl and alkylene and alkoxy of 1 to 6 carbon atoms and alkoxyalkoxy of 2 to 6 carbon atoms and optionally disubstituted with at least one member of the group consisting of epoxy, methylene and alkylene dioxy and alkylenedithio and alkyleneoxythio of 1 to 3 carbon atoms.

2. A compound of claim 1 wherein $R_3$ is selected from the group consisting of alkyl of 1 to 10 carbon atoms and phenyl and naphthyl optionally substituted with at least one member of the group consisting of halogen, alkyl of 1 to 6 carbon atoms and alkoxy of 1 to 6 carbon atoms.

3. A compound of claim 1 wherein $R_3$ is selected from the group consisting of phenyl, p-methoxyphenyl and p-methylphenyl.

4. A compound of claim 1 having at least one double bond selected from the group consisting of 1(2), 3(4), 4(5), 5(6), 6(7), 9(11) and 11(12).

5. A compound of claim 1 having at least one substituent selected from the group consisting of hydroxy at 3-, 9-, 11-, 12- and 14-positions, keto at 3,- 11- and 12-positions, fluorine, chlorine and bromine in the 6-, 9- and 11-positions, methyl in the 1- and 6-positions, alkoxy of 1 to 4 carbon atoms in the 3-, 9- and 11-positions and alkoxyalkoxy of 2 to 6 carbon atoms in the 3- and 11-positions.

6. A compound of claim 1 having at least one substituent selected from the group consisting of 1,2-epoxy, 9,11-epoxy, 1,2-methylene, and 3,3-alkylenedioxy, 3,3-alkylenedithio and 3,3-alkyleneoxythio of 1 to 3 alkylene carbon atoms.

7. A compound of the formula

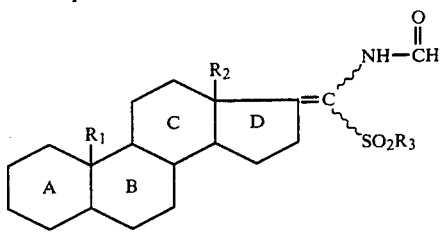

wherein $R_1$ is selected from the group consisting of hydrogen and alkyl of 1 to 4 carbon atoms or may form a double bond in the 1(10), 5(10) or 9(10) position, $R_2$ is selected from the group consisting of hydrogen and alkyl of 1 to 4 carbon atoms, $R_3$ is selected from the group consisting of alkyl of 1 to 10 carbon atoms, dialkylamino of 1 to 8 alkyl carbon atoms, heterocycle of 4 to 8 atoms optionally containing an oxygen atom and aryl optionally substituted with at least one member of the group consisting of halogen and alkyl and alkoxy of 1 to 6 carbon atoms and the A,B,C and D rings may contain at least one double bond and may be optionally substituted with at least one member of the group consisting of hydroxy, amino, oxygen, halogen, alkyl and alkylene and alkoxy of 1 to 6 carbon atoms and alkoxyalkoxy of 2 to 6 carbon atoms and optionally disubstituted with at least one member of the group consisting of epoxy, methylene and alkylenedioxy and alkylenedithio and alkyleneoxythio of 1 to 3 carbon atoms.

8. A compound of claim 7 wherein $R_3$ is selected from the group consisting of alkyl of 1 to 10 carbon atoms and phenyl and naphthyl optionally substituted with at least one member of the group consisting of halogen, alkyl of 1 to 6 carbon atoms and alkoxy of 1 to 6 carbon atoms.

9. A compound of claim 7 wherein $R_3$ is selected from the group consisting of phenyl, p-methoxyphenyl and p-methylphenyl.

10. A compound of claim 7 having at least one double bond selected from the group consisting of 1(2), 3(4), 4(5), 5(6), 6(7), 9(11) and 11(12).

11. A compound of claim 7 having at least one substituent selected from the group consisting of hydroxy at 3-, 9-, 11-, 12- and 14-positions, keto at 3-, 11- and 12-positions, fluorine, chlorine and bromine in the 6-, 9- and 11-positions, methyl in the 1- and 6-positions, alkoxy of 1 to 4 carbon atoms in the 3-, 9- and 11-positions and alkoxyalkoxy of 2 to 6 carbon atoms in the 3- and 11-positions.

12. A compound of claim 7 having at least one substituent selected from the group consisting of 1,2-epoxy, 9,11-epoxy, 1,2-methylene and 3,3-alkylenedioxy, 3,3-alkylenedithio and 3,3-alkyleneoxythio of 1 to 3 alkylene carbon atoms.

* * * * *